US009161972B2

(12) United States Patent
Olivares-Fuster et al.

(10) Patent No.: US 9,161,972 B2
(45) Date of Patent: Oct. 20, 2015

(54) MODIFIED LIVE FLAVOBACTERIUM STRAINS, STABILIZED VACCINES COMPRISING SAME, AND METHODS OF MAKING AND USE THEREOF

(71) Applicant: Auburn University, Auburn, AL (US)

(72) Inventors: Oscar Olivares-Fuster, Opelika, AL (US); Covadonga R. Arias, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 14/169,976

(22) Filed: Jan. 31, 2014

(65) Prior Publication Data

US 2014/0220077 A1    Aug. 7, 2014

Related U.S. Application Data

(60) Provisional application No. 61/759,821, filed on Feb. 1, 2013, provisional application No. 61/773,468, filed on Mar. 6, 2013.

(51) Int. Cl.
| | | |
|---|---|---|
| *A61K 39/02* | (2006.01) | |
| *A61K 47/02* | (2006.01) | |
| *A61K 39/00* | (2006.01) | |

(52) U.S. Cl.
CPC ............. *A61K 39/0208* (2013.01); *A61K 47/02* (2013.01); *A61K 2039/522* (2013.01); *A61K 2039/552* (2013.01)

(58) Field of Classification Search
None
See application file for complete search history.

(56) References Cited

U.S. PATENT DOCUMENTS 4,708,871 A    11/1987    Geysen

OTHER PUBLICATIONS

Olivares-Fuster et al. (J. Fish Dis., 34:385-394, 2011).*
Arias C R et al. Genetic fingerprinting of Flavobacterium columnare isolates from cultured fish. Journal of Applied Microbiology 2004; 97(2):421-8.
Bondad-Reantaso M G et al. Disease and health management in Asian aquaculture. Veterinary Parasitology 2005; 132 (3):249-72.
Decostere A et al. Shieh medium supplemented with tobramycin for selective isolation of Flavobacterium columnare (Flexibacter columnaris) from diseased fish. Journal of clinical microbiology 1997; 35(1):322-4.
Evensen O. Development in fish vaccinology with focus on delivery methodologies, adjuvants and formulations. Options Mediterraneennes 2009; 86:177-86.
Klesius P H et al. Flavobacterium columnare chemotaxis to channel catfish mucus. Ferns Microbiology Letters Nov. 2008; 288(2):216-20.
McCallum N et al. In vivo survival of teicoplanin-resistant Staphylococcus aureus and fitness cost of teicoplanin resistance. Antimicrobial agents and chemotherapy 2006; 50(7):2352-60.
Olivares-Fuster O et al. Host-specific association between Flavobacterium columnare genomovars and fish species. Systematic & Applied Microb. 2007; 30(8):624-33.
Shoemaker C A et al. Flavobacterium columnare genomovar influences mortality in channel catfish (Ictalurus punctatus). Veterinary Microbiology Mar. 2008; 127(3-4):353-9.
Thomas-Jinu S, Goodwin A. Morphological and genetic characteristics of Flavobacterium columnare isolates: correlations with virulence in fish. Journal of Fish Diseases 2004; 27(1):29-35.
Amend, Donald F., "Potency Testing of Fish Vaccines", International Symposium in Fish Biologies, 447-454, 1981.
Bader, Joel A. et al., "Rapid detection of columnaris disease in channel catfish (Ictalurus punctatus) with a new species-specific 16-S rRNA gene based PCR primer for Flavobacterium columnare", Journal of Microbiological Methods, 52: 209-220, 2003.
Darwish, Ahmed M., et al., "Genentic diversity of Flavobacterium columnare examined by restriction fragment length polymorphism and sequencing of the 16S ribosomal RNA gene and the 16S-23S rDNA spacer", Molecular and Cellular Probes, 19: 267-274, 2005.
Griffin, B.R., "Columnaris Disease: Recent Advances in Research", Aquaculture Magazine, May/June, 48-50, 1987.
Khoo, Lester, "Annual Fish Diagnostic Laboratory Report for 2000", NWAC News, Jul. 6-7, 2001.
Kirkland, Sandi, "Evaluation of the Live-Attenuated Vaccine AquaVac-COL on Hybrid Channel x Blue Catfish Fingerlings in Earthen Ponds", Auburn University, Dec. 13, 2010.
Klesius, Phillip H. et al., "Development and Use of Modified Live Edwardsiella ictaluri Vaccine against Enteric Septicemia of Catfish", Advances in Veterinary Medicine, 41: 523-537, 1999.
Mississippi State University, "2010 Annual Case Summary Report Aquatic Research & Diagnostic Laboratory", College of Veterinary Medicine, 2010.
Olivares-Fuster, Oscar et al., "Adhesion dynamics of Flavobacterium columnare to channel catfish Ictalurus punctatus and zebrafish Danio rerio after immersion challenge", Disease of Aquatic Organisms, 96: 221-227, 2011.
Olivares-Fuster, Oscar et al., "Development and characterization of rifampicin-resistant mutants from high virulent strains of Flavobacterium columnare", Journal of Fish Diseases, 34: 385-394, 2011.
Schachte, John H., "Columnaris Disease", Great Lakes Fishery Commission, Chapter 23, 199-203. 2015.
Schurig, Gerhardt G. et al., "Biological properties of RB51; a stable rough strain of Brucella abortus", Veterinary Microbiology, 28: 171-188, 1991.
Shoemaker, Craig A. et al., "Immunization of eyed channel catfish, Ictalurus punctatus, eggs with monovalent Flavobacterium columnare vaccine and bivalent F. columnare and Edwardsiella ictaluri vaccine", Vaccine, 25: 1126-1131, 2007.
Triyanto et al., "Genotypic Diversity of Strains of Flavobacterium columnare from Diseased Fishes", The Japanese Society of Fish Pathology, 34:2, 65-71, 1999.
Wagner, Bruce A. et al., "The Epidemiology of Bacterial Diseases in Food-Size Channel Catfish", Journal of Aquatic Animal Health, 14:4, 263-272, 2002.

* cited by examiner

*Primary Examiner* — Brian J Gangle
(74) *Attorney, Agent, or Firm* — Andrus Intellectual Property Law, LLP

(57) ABSTRACT

The present invention provides attenuated *F. columnare* strains that elicit an immune response in an animal, particularly a fish, against virulent *F. columnare* compositions comprising said strains, methods of vaccination against *F. columnare*, and kits for use with such methods and compositions. The invention further relates to a stabilization buffer, which allows the attenuated compositions to remain storage stable at ambient temperatures for extended periods of time.

15 Claims, 3 Drawing Sheets

MODIFIED LIVE FLAVOBACTERIUM STRAINS, STABILIZED VACCINES COMPRISING SAME, AND METHODS OF MAKING AND USE THEREOF

INCORPORATION BY REFERENCE

This application claims priority to provisional applications U.S. Ser. No. 61/759,821, filed on Feb. 1, 2013, and U.S. Ser. No. 61/773,468, filed on Mar. 6, 2013, which are incorporated by reference herein in their entirety. All references cited herein, and references cited therein, are herein incorporated by reference in their entirety.

FIELD OF THE INVENTION

The present invention relates generally to attenuated bacterial vaccines, particularly those providing broad, safe, and effective protection to fish against infections/disease caused by *Flavobacterium* spp., including *Flavobacterium columnare* (*F. columnare*). The invention further relates to methods of producing the attenuated bacteria, and to the identification of nucleic acid variations that are associated with decreased virulence of the attenuated bacteria. The invention also relates to stabilization buffers, and methods of use thereof, for stabilizing the disclosed attenuated bacteria.

The invention accordingly relates to stabilized immunogenic or vaccine compositions comprising the bacteria of the invention; e.g., live attenuated bacteria. The bacteria also could be inactivated in the compositions; but it is particularly advantageous that the bacteria be live attenuated *Flavobacterium* spp. bacteria. The invention therefore further relates to methods for preparing and/or formulating such compositions; e.g., culturing or growing or propagating the bacteria on or in suitable medium, harvesting the bacteria, optionally inactivating the bacteria, and optionally admixing the bacteria with a suitable veterinarily or pharmaceutically acceptable carrier, excipient, diluent or vehicle and/or an adjuvant and/or stabilizer. Thus, the invention also relates to the use of the bacteria in formulating such compositions.

BACKGROUND OF THE INVENTION

*Flavobacterium columnare*, a causative agent of columnaris disease, causes great annual economic losses for the cultured catfish industry in the United States and many other cultured fish species [1]. It has been recognized as a worldwide pathogen of freshwater fishes affecting wild, cultured and ornamental fish populations including the commercially important species [2-4]. Epizootics of columnaris disease frequently occur in natural populations and have been devastating/troublesome in fish farms, hatcheries, ponds, pens and cages particularly in fishes held under intensive culture conditions with poor water quality [5]. In the catfish industry, columnaris disease is the leading cause of catfish mortality, in-pond mortality rates among adults and fingerlings can reach 60 and 90%, respectively [6]. Columnaris is one of the most frequently occurring disease in catfish, representing an average of 41% of the total cases submitted for diagnosis from 2001 to 2010 [7]. Columnaris disease or mixed infections including columnaris is considered the greatest cause of economic loss on catfish farms by more than 70% of the catfish farmers polled in the four leading catfish-producing states [8]. Catfish at any age, during all seasons, and under variety of water conditions are susceptible to columnaris infection [9].

The intensification of aquaculture operations has increased the incidence of infectious diseases [10]. Sustainable development of aquaculture relies on disease prevention and vaccination has become the best tool to achieve that goal. Effective vaccines are ultimately the safest prophylactic approach to evade infectious diseases. Moreover, the use of antibiotics in aquaculture has been reduced dramatically since the introduction of vaccines [11].

*F. columnare* is a genetically heterogeneous group of pathogens, divided into three main different genomovars and genetically different strains within the species demonstrate various levels of virulence for different fish species [12-15]. Genomovar II strains were found to be significantly more virulent to channel catfish than genomovar I strains and have higher adhesion capacity as well [14, 16]. Rifampicin resistance strategy has been successfully used to develop modified live attenuated bacterial vaccines for commercial use in aquaculture [17, 18]. Currently, a modified live *F. columnare* vaccine is available for commercial use to prevent columnaris disease under the licensed name AQUAVAC-COL™. The active ingredient in this vaccine is an avirulent rifampicin-resistant mutant of *F. columnare* genomovar I, the less virulent group. The efficacy of this vaccine has been publically questioned from farm settings. Recently, inventors have developed safe, and permanently stable, rifampicin-resistant mutants from genomovar II strains, the highly virulent group. Since genomovar II strains are more virulent, a specific vaccine targeting this genomovar is likely to increase the protective effect of vaccination.

Therefore, the purpose of this study was to evaluate the efficacy in zebrafish, channel catfish, and Nile tilapia of the new modified live *F. columnare* vaccines (mutants) developed by repeated passage of virulent genomovar II strains on a medium containing increasing concentrations of rifampicin. It is thus a primary object of the instant disclosure to provide a safe and effective *F. columnare* vaccine.

REFERENCES

[1] Wagner B A et al. The epidemiology of bacterial diseases in food-size channel catfish. Journal of Aquatic Animal Health 2002; 14(4):263-72.

[2] Austin B, Austin D A. Bacterial fish pathogens: disease of farmed and wild fish: Springer Verlag, 1999.

[3] Bader J A et al. Rapid detection of columnaris disease in channel catfish (*Ictalurus punctatus*) with a new species-specific 16-S rRNA gene-based PCR primer for *Flavobacterium columnare*. Journal of Microbiological Methods 2003; 52(2):209-20.

[4] Thomas-Jinu S, Goodwin A. Morphological and genetic characteristics of *Flavobacterium columnare* isolates: correlations with virulence in fish. Journal of Fish Diseases 2004; 27(1):29-35.

[5] Schachte J H. Columnaris disease. A guide to integrated fish health management in the Great Lakes basin Great Lakes Fishery Commission, Special Publication 1983(83-2):199-203.

[6] Plumb J A. Health maintenance and principal microbial diseases of cultured fishes: Iowa State University Press, Ames, Iowa, 1999.

[7] MSU. 2010 Annual Case Summary Report, Aquatic Research and Diagnostic Laboratory, Mississippi State University, Stoneville, Miss. tcnwac.msstate.edu/cvm2010.pdf.

[8] Khoo L. Annual fish diagnostic laboratory report for 2000. NWAC News 2001; 4(1):6-7.

[9] Griffin B. Columnaris disease: recent advances in research. Aquacult. '87; 13:48-50.

[10] Bondad-Reantaso M G et al. Disease and health management in Asian aquaculture. Veterinary Parasitology 2005; 132(3):249-72.

[11] Evensen O. Development in fish vaccinology with focus on delivery methodologies, adjuvants and formulations. Options Mediterraneennes 2009; 86:177-86.

[12] Arias C R et al. Genetic fingerprinting of *Flavobacterium columnare* isolates from cultured fish. Journal of Applied Microbiology 2004; 97(2):421-8.

[13] Darwish A M, Ismaiel A A. Genetic diversity of *Flavobacterium columnare* examined by restriction fragment length polymorphism and sequencing of the 16S ribosomal RNA gene and the 16S-23S rDNA spacer. Molecular and Cellular Probes 2005; 19(4):267-74.

[14] Shoemaker C A et al. *Flavobacterium columnare* genomovar influences mortality in channel catfish (*Ictalurus punctatus*). Veterinary Microbiology 2008 March; 127 (3-4):353-9.

[15] Triyanto A, Wakabayashi H. Genotypic diversity of strains of *Flavobacterium columnare* from diseased fishes. Fish Pathology 1999; 34:65-71.

[16] Olivares-Fuster O, Bullard S A, McElwain A, Llosa M J, Arias C R. Adhesion dynamics of *Flavobacterium columnare* to channel catfish *Ictalurus punctatus* and 15 zebrafish *Dania rerio* after immersion challenge. Diseases of Aquatic Organisms 2011; 96(3):221.

[17] Klesius P H, Shoemaker C A. Development and use of modified live *Edwardsiella ictaluri* vaccine against enteric septicemia of catfish. Advances in Veterinary Medicine 1999; 41:523-37.

[18] Shoemaker C A et al. Immunization of eyed channel catfish, *Ictalurus punctatus*, eggs with monovalent *Flavobacterium columnare* vaccine and bivalent *F. columnare* and *Edwardsiella ictaluri* vaccine. Vaccine 2007; 25(6): 1126-31.

[19] Schurig G G et al. Biological properties of RB51; a stable rough strain of *Brucella abortus*. Veterinary Microbiology 1991; 28(2):171-88.

[20] Olivares-Fuster O, Arias C R. Development and characterization of rifampicin resistant mutants from high virulent strains of *Flavobacterium columnare*. Journal of Fish Diseases 2011 May; 34(5):385-94.

[21] Decostere A et al. Shieh medium supplemented with tobramycin for selective isolation of *Flavobacterium columnare* (Flexibacter columnaris) from diseased fish. Journal of clinical microbiology 1997; 35(1):322-4.

[22] Amend D F. Potency testing of fish vaccines. Fish biologics: serodiagnostics and vaccines 1981.

[23] Klesius P H et al. *Flavobacterium columnare* chemotaxis to channel catfish mucus. Ferns Microbiology Letters 2008 November; 288(2):216-20.

[24] Kirkland S. Evaluation of the Live-Attenuated Vaccine AquaVac-COL® on Hybrid Channel×Blue Catfish Fingerlings in Earthen Ponds: Auburn University; 2010.

[25] McCallum N et al. In vivo survival of teicoplanin-resistant Staphylococcus aureus and fitness cost of teicoplanin resistance. Antimicrobial agents and chemotherapy 2006; 50(7):2352-60.

[26] Shoemaker C A et al. *Flavobacterium columnare* genomovar influences mortality in channel catfish (*Ictalurus punctatus*). Veterinary Microbiology 2008; 127 353-9.

[27] Olivares-Fuster O et al. Host-specific association between *Flavobacterium columnare* genomovars and fish species. Systematic & Applied Microb. 2007; 30(8):624-33.

SUMMARY OF THE INVENTION

The present invention relates to new attenuated strains of *F. columnare*, which are capable of providing fish with safe, effective, and broad protective immunity. Relative to a virulent parental strain, the disclosed attenuated strains have one or more genetic variations, including insertions, deletions and substitutions, whose presence is associated with reduced virulence.

A further object of this invention is to provide safe and effective *F. columnare* vaccine compositions, as well as methods for treatment and prophylaxis of infection by *F. columnare*. In particular, the compositions may further comprise a stabilization buffer, which contains a combination of salts, including, for example, sulfates, chlorides, and phosphates. The buffer may allow the bacteria to remain viable for extended periods of time, including up to at least about one year, or greater. In an ideal embodiment, the buffer allows such extended storage stability at a variety of temperatures, including room temperature, which may be around 65 to 75° F., or higher temperatures, such as those that may be routinely encountered during shipping and storage of immunological compositions. In a specific embodiment, the buffer contains iron sulfate, calcium chloride, potassium phosphate monobasic, and magnesium sulfate, in amounts sufficient to provide the extended storage stability.

The invention further provides methods for inducing in a fish an immune—including protective—response against *F. columnare*, as well as methods for preventing or treating *F. columnare*, or disease state(s) caused by *F. columnare*, comprising administering the attenuated strains, or a composition comprising the attenuated strains to fish in need thereof. Kits comprising at least one attenuated *F. columnare* strain and instructions for its use are also provided.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein.

DETAILED DESCRIPTION OF THE INVENTION

Figure 1:
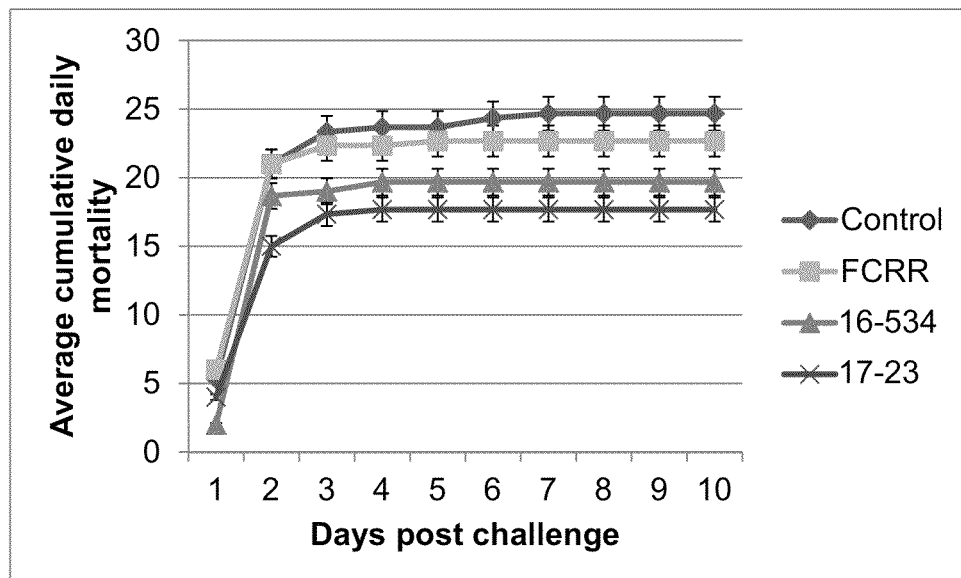
FIG. 1 shows average/mean cumulative daily mortality of zebrafish immersion vaccinated with 17-23, 16-534, FCRR or sham vaccinated and immersion challenged at 28 dpv with BGFS-27 (virulent genomovar II strain of *F. columnare*), cumulative mortalities were calculated from vaccination trial 1.

The present invention provides attenuated *F. columnare*, useful in the production of vaccines for protecting fish against Columnaris disease. The present invention also encompasses *Flavobacterium* products (e.g., proteins, antigens, immunogens, epitopes), which are encoded by nucleotide sequences present within the attenuated bacteria. Said nucleotides and products may be useful for preparing vaccine or immunogenic compositions, and/or for eliciting an immune response, including a protective immune response.

The attenuated *F. columnare* mutants were produced by serial passaging of virulent parental strains, as described in Olivares-Fuster and Arias, 2011 [20]. Briefly, to obtain the attenuated strains, four *F. columnare* isolates were initially cultured in rifampicin-supplemented MS agar plates (50 µg mL$^{-1}$). Single colonies were picked and placed onto the next concentration of rifampicin (100 µg mL$^{-1}$). Subsequent serial transfers were performed at 150, 200, 250 and 300 µg mL$^{-1}$ rifampicin. A skilled person using routine work can carry out the methods plainly disclosed in Olivares-Fuster to produce additional attenuated mutants, which may be included in immunological composition according to the instant disclosure. As discussed herein, "attenuation" reduces or abolishes the pathogenicity of the bacteria and the gravity of the clinical signs or lesions, decreases the growth rate of the bacteria, and prevents the death from the bacteria.

In an embodiment, the attenuated *Flavobacterium* spp. mutants are useful for the production of live attenuated immunogenic compositions, or live attenuated vaccines, having a high degree of safety and immunogenicity. In a particular embodiment, the present invention encompasses attenuated *F. columnare* strains and vaccines comprising the same, which elicit an immunogenic response in an animal, particularly the attenuated *F. columnare* strains that elicit, induce or stimulate a response in a fish.

In an embodiment, the invention provides a safe and effective immunological composition comprising at least one attenuated strain of a genomovar II *Flavobacterium* spp., wherein the attenuated strain is resistant to rifampicin, and wherein the attenuated strain is capable of eliciting an immune response in fish against a subsequent natural exposure to, or experimental challenge with, at least one virulent *Flavobacterium* ssp. strain. In a particular embodiment, the immune response is a protective immune response.

In a particular embodiment, the attenuated *F. columnare* strain has substantially the same mutations and rifampicin resistance, relative to its virulent parental strain, as the 17-23 strain, which was deposited at the Colección Española de Cultivos TIPO (CECT), Universidad de Valencia, Edificio de Investigación. Campus de Buriassot, 4600 Burgassot (Valencia) España, as International Depository Authority on Jun. 25, 2010 under the Accession number given by the International Depository Authority: CECT-7737. These mutations result in the attenuated strain having reduced virulence relative to its virulent parental strain.

In an embodiment, the attenuated strain is the 17-23 strain, which was deposited as CECT-7737 at the Colección Española de Cultivos TIPO (CECT). Universidad de Valencia. Edificio de Investigación. Campus de Buriassot, 4600 Burgassot (Valencia) España, as International Depository Authority on Jun. 25, 2010.

In another particular embodiment, the attenuated *F. columnare* strain has substantially the same mutations and rifampicin resistance, relative to its virulent parental strain, as the 16-534 strain, which was deposited at the Colección Española de Cultivos TIPO (CECT), Universidad de Valencia, Edificio de Investigación. Campus de Buriassot, 4600 Burgassot (Valencia) España. as International Depository Authority on Jun. 25, 2010 under the Accession number. These mutations result in the attenuated strain having reduced virulence relative to its virulent parental strain.

In an embodiment, the attenuated strain is the 16-534 strain, which is deposited as CECT-7736 at the Colección Española de Cultivos TIPO (CECT). Universidad de Valencia, Edificio de Investigación, Campus de Buriassot, 4600 Burgassot (Valencia) España. as International Depository Authority on Jun. 25, 2010.

In another embodiment, the invention provides a safe and effective immunological composition, comprising at least one attenuated strain of a genomovar II *Flavobacterium* spp., wherein the attenuated strain is resistant to rifampicin.

In an embodiment, the composition is a vaccine composition, which is capable of eliciting a protective immune response in fish against a subsequent natural exposure to, or experimental challenge with, at least one virulent *F. columnare* strain.

In another embodiment, the at least one virulent *F. columnare* is either a genomovar group I, II or both.

In an embodiment, the attenuated *Flavobacterium* ssp. is *F. columnare*.

In another embodiment, the vaccine comprises an attenuated strain having substantially the same antigenic profile as the *Flavobacterium* strain deposited as CECT 7737.

In yet another embodiment, the vaccine composition comprises an attenuated strain deposited in the International Depository Authority as CECT-7737.

Any of the preceding compositions may further comprise a pharmaceutically or veterinarily acceptable carrier.

In a particular embodiment, the compositions further comprise a stabilization buffer. The buffer may comprises mineral salts, including sulfates, chlorides, and phosphates. In one embodiment, the buffer comprises $FeSO_4$, $CaCl_2$, $KH_2PO_4$, and $MgSO_4$. The skilled person will be able to make adjustments to the precise amounts of these buffer components, using non-routine optimization, to suit specific purposes. However, one particularly useful stabilization buffer comprises about 0.4 µM $FeSO_4$, about 4.6 µM $CaCl_2$, 100 µM $KH_2PO_4$, and about 120 µM $MgSO_4$. As used herein, "about" means "±10%" around the recited quantity. For example, "about 100 µM" encompasses 90 to 110 µM. In an embodiment, the salts are mixed and autoclaved following standard techniques for liquid sterilization (e.g. 121° C., 1 atmosphere, and for at least about twenty minutes).

In another embodiment, the addition of the buffer to the immunological composition(s) stabilizes the composition(s) for at least about twelve months, when the compositions are stored at about room temperature or up to about 30° C. It is expected the buffered immunological compositions may remain viable at these and other temperatures, which might occur during routine shipping and storage of such immunological compositions.

In a particular embodiment, the buffer is useful for storage of live cells at room temperature.

The invention also encompasses a method of storing live cells, including live attenuated *Flavobacterium* cells, for extended periods of time comprising the steps of storing the live cells in the herein disclosed stabilization buffer.

In an embodiment, the storing method comprises the steps of pelleting the live cells by routine centrifugation techniques, for example, at approximately 5,000 rpm for 5 minutes, removing the supernatant, re-suspending the cells in the storage buffer, and transferring the cells to a sterile container, thereby storing the cells.

In a particular embodiment, the cells are grown in an appropriate culture medium, pelleted at ~5,000 rpm for about five minutes, and the culture medium is then removed. The cells are then resuspended gently (no vortexing) and transferred to a sterile container, leaving an air chamber of at least the same volume as the liquid. The container may be sealed with a cap. Where previously *Flavobacterium* spp. could only be preserved using freezing techniques, the present disclosure provides buffered compositions with enhanced storage stability. Instead of dying after only 24 to 36 hours (liquid culture medium) or only 48 to 72 hours (solid culture medium), the disclosed, buffer-stabilized, *Flavobacterium* spp. remain stable for at least two months at room temperature, greatly reducing the storage and shipping costs of the compositions.

The invention further encompasses a method of inducing protective immunity in fish against exposure to, or experimental challenge with, virulent strains of genomovar I or II *Flavobacterium* spp. In an embodiment, the induction method comprises the step of administering to said fish the disclosed immunological or storage-stable immunological compositions, thereby inducing the protective immunity.

In an embodiment, the virulent strain is either a genomovar I or II *F. columnare.*

In an embodiment, the induction method is practiced on freshwater fish.

In another embodiment, the fish is a tilapia, a catfish, a zebrafish, a salmon, a trout, a carp, a tuna, a shellfish, or any other fish capable of being farmed in an aquaculture setting.

In some embodiments, the administration is by immersion vaccination.

In another aspect, the novel attenuated *F. columnare* strains are formulated into safe, effective vaccine against *F. columnare* and infections/diseases cause by *F. columnare.*

In an embodiment, these mutants may also be used as vectors, such that the mutants carry and express in vivo an additional, non-native antigen (e.g. heterologous gene or gene fragment).

By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes fish, reptiles, avians, mammals (including humans). The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), fish (e.g., tilapia, catfish, zebrafish and salmon), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Compositions

The present invention relates to attenuated *Flavobacterium* spp., including *F. columnare*, vaccines or immunological compositions, which may comprise an attenuated *F. columnare* strain and a pharmaceutically or veterinarily acceptable carrier, excipient, or vehicle, which elicits, induces or stimulates a response in an animal.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Methods of Use and Article of Manufacture

The present invention includes the following method embodiments. In an embodiment, a method of vaccinating an animal comprising administering a composition comprising at least one attenuated *F. columnare* strain(s) and a pharmaceutical or veterinarily acceptable carrier, excipient, or vehicle to an animal is disclosed. In one aspect of this embodiment, the animal is a fish. In a particular embodiment, the fish is a tilapia, a zebrafish, a catfish, or a salmon.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation. For fish, immersion vaccination is a preferred route of administration.

Another embodiment of the invention is a kit for performing a method of eliciting or inducing an immunological or protective response against *F. columnare*, in an animal comprising an attenuated *F. columnare* immunological composition or vaccine and instructions for performing the method of delivering an effective amount for eliciting an immune response in the animal.

Another embodiment of the invention is a kit for performing a method of inducing an immunological or protective response against the *F. columnare* in an animal comprising a composition or vaccine comprising the attenuated *F. columnare* strain of the invention, and instructions for performing the method of delivery in an effective amount for eliciting an immune response in the animal.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cationic lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The invention will now be further illustrated by the following non-limiting Examples.

EXAMPLES

Materials and Methods. Fish Husbandry.

Non-sexed adult zebrafish, *Dania rerio*, (n=360, mean weight=0.45±0.04 g) were purchased from Aquatica Tropicals (Plant City, Fla., USA), transferred to the Aquatic Microbiology Laboratory (AML), and housed in twelve aquaria (nine gallons/each) at 30 fish per tank. Prior to vaccination, two zebrafish were randomly selected from each aquarium, homogenized, and microbiologically examined (plated on modified Shieh (MS) agar with tobramycin). The homogenized pools were proved culture-negative for the presence of *F. columnare*. In the same way, one month old channel catfish fry, *Ictalurus punctatus*, (n=480; mean weight=0.05±0.003 g) were supplied by Dr. Newton, the fish were transferred to the AML, and housed in the same system at forty fish per tank. Prior to vaccination, five catfish fry were randomly selected from each aquarium, homogenized, and microbiologically examined as mentioned earlier. The homogenized pools were proved culture-negative for the presence of *F. columnare*. Similarly, 6 month old all male Nile tilapia fingerlings, *Oreochromis niloticus*, (n=600, mean weight=9.4±0.5 g) were obtained from E. W. Shell Fisheries Center, North Auburn Fisheries experiment Station. After preliminary acclamation, the fish were moved from a big tank and placed into thirty aquaria (nine gallons/each) at twenty fish per tank.

Prior to vaccination, three fish were randomly selected from each aquarium, microbiologically examined by streaking on modified Shieh (MS) agar tobramycin plates from the skin and gills and were verified culture-negative for the presence of *F. columnare*. Zebrafish, channel catfish and Nile tilapia were acclimated to lab conditions for two weeks before the vaccination date and fed daily to apparent satiation with commercial dry fish food AQUAMAX Grower 300, I 00 and 400 (Purina Mills), respectively. Each aquarium used is a closed circulating system and was equipped with bio-filter, heater and air stone, and supplied with artificial fresh-chlorine free water (80 ppm alkalinity, 70 ppm hardness). Temperature was kept at 27±1° C. and pH at 7.6±0.2. Fish were subjected to a 12 h light: 12 h dark photoperiod. Water quality parameters were checked every other day. Ammonia and nitrite levels were undetectable throughout the study period. At the time of vaccination, aquaria were assigned blindly to each treatment group.

Bacterial Strains and Growth Conditions.

The rifampicin resistant *F. columnare* mutants used in these experiments were generated by using the rifampicin resistance strategy following a modification of the protocol originally used with *Brucella abortus* [19]. These mutants were obtained from genetically different genomovar II strains. The alterations in the lipopolysaccharide and protein profiles of these mutants were studied accompanied by complete genetic and phenotypic characterization [20]. All *F. columnare* strains used in this study were stored at −80° C. as glycerol stocks and were cultured on MS agar or in MS broth with shaking at 100 rpm at 28° C. for 24 h. Plate counts of each strain (in triplicates) were performed to calculate the average number of colony forming units per milliliter (CFU/mL) of bacteria used to vaccinate or to challenge fish as reported under each experiment. *F. columnare* mutants were confirmed still resistant to rifampicin by plating on MS agar medium containing 200 μg/mL rifampicin before each vaccination (three experiments were conducted, one with each fish species).

Following each challenge experiment, *F. columnare* was isolated from the dead fish by plating on MS agar medium containing 1 μg/mL tobramycin [21]. Putative *F. columnare* colonies were identified based on their pigmentation and characteristic morphology of the colonies on agar plates.

Statistical Analysis.

Mortality data were analyzed by one-way analysis of variance (ANOVA) using general linear model (PROC GLM) followed by Duncan's multiple range test (SAS Institute, Cary, N.C.) to determine significant differences (P<0.05) between the mean mortality of treatment groups and replicates (aquaria) in trials 1, and 2. For trial three, Tukey's Studentized Range (HSD) test for all-pairwise comparisons was used to determine significant (p<0.05) difference between vaccinated (either with the experimental vaccines genomovar II or FCRR) and non-vaccinated fish challenged with either genomovar I or genomovar II *F. columnare*.

Results.

The new rifampicin resistant *F. columnare* genomovar II mutants were safe to use as vaccine in zebrafish, channel catfish and tilapia in all the trials, as no mortalities were recorded during the vaccination periods. When the vaccinated fish were challenged with virulent *F. columnare* strain at 28 dpv, results of challenges were presented as cumulative mortality (% mortality) and as RPS as described previously [22].

Cumulative mortality was calculated by dividing number of dead fish per time period by the total mm1ber of fish per treatment and multiplying by 100. RPS was calculated according to the following formula: RPS=[1−(vaccinated mortality/control mortality)]×100.

Example 1

Zebrafish Vaccination and Challenge

A total of 336 adult zebrafish were vaccinated by DI in a 2 L bath containing the experimental vaccines 17-23 and 16-534, or in FCRR (the active ingredient used in the commercial vaccine, AQUAVAC-COL™) at concentrations of $7.8\times10^6$, $1.5\times10^6$ or $9.1\times10^6$ CFUml$^{-1}$, respectively, for thirty min. A control group was sham vaccinated by immersion in sterile MS broth and exposed to the same procedures and the same environmental conditions as the vaccinated fish except for the addition of an active vaccine ingredient. Four treatments/three replicates each. After vaccination, the fish in each treatment group were removed from the vaccine bath, replaced back into their holding aquaria according to their respective treatment groups until challenge, and daily fed 2% body weight. At 28 dpv, both vaccinated and sham vaccinated fish were immersion challenged in a 2 L bath containing highly virulent *F. columnare* strain (BGFS-27, genomovar II) at a concentration of $6.4\times10^6$ CFUml$^{-1}$ for thirty minutes following standard protocols. Feeding was resumed 24 h post challenge. Challenged fish were monitored in each tank for fifteen days. Dead fish exhibiting typical signs of columnaris disease, including saddleback and gill lesions, were removed twice a day and cultured as described above to re-isolate and confirm *F. columnare* as the cause of death. *F. columnare* was recovered from all the dead fish.

The cumulative mortality observed in the sham vaccinated zebrafish after 15 days post challenge was 88.1%, which was significantly higher ($p<0.05$) when compared to the cumulative mortality of 63.1% in fish vaccinated with the genomovar II mutant (17-23) (Table 1). The cumulative mortalities 63.1 and 70.2% observed in fish vaccinated with both genomovar II mutants 17-23 and 16-534, respectively, were lower than 81.0% observed in fish vaccinated with the genomovar I mutant of the commercial vaccine (FCRR) (FIG. 1). Although both genomovar II mutants resulted in a lower cumulative mortality than the genomovar I mutant of the commercial vaccine, only 17-23 showed a significantly lower cumulative mortality than FCRR, suggesting that these new genomovar II mutants 9 provided higher protection to zebrafish against virulent wild type *F. columnare* strain than provided by the genomovar I mutant. Relative percent survival (RPS) was 28.4, 20.3 and 8.1% in the fish vaccinated with 17-23, 16-534 and FCRR, respectively (Table 1). Following challenge, all the dead fish were confirmed positive for *F. columnare* as the cause of death by culturing.

TABLE 1

Cumulative mortality (mean ± S.E.) and relative percent survival of vaccinated zebrafish after immersion challenge with virulent *F. columnare* strain at 28 dpv (trial 1). Within a column, different superscript letters indicates significant difference ($p < 0.05$).

| Vaccine | Vaccination route | Vaccine dose | Challenge Strain & dose | No. Dead/ challenged | Mortality (%) ± SE | RPS[b] (%) |
|---|---|---|---|---|---|---|
| 17-23 | DI[a] | $7.8 \times 10^6$ CFU/mL | BGFS-27 (Genomovar II) | 53/84 | $63.1 \pm 0.38$ [A] | 28.4 |
| 16-534 | DI[a] | $1.5 \times 10^6$ CFU/mL | $6.4 \times 10^6$ CFU/mL | 59/84 | $70.2 \pm 0.87$ [AB] | 20.3 |
| FCRR | DI[a] | $9.1 \times 10^6$ CFU/mL | | 68/84 | $81.0 \pm 0.32$ [AB] | 8.1 |
| Control | DI[a] | Sham vaccinated | | 74/84 | $88.1 \pm 1.8$ [B] | — |

[a]DI, direct immersion

[b]RPS, relative percent survival

Example 2

Channel Catfish Fry Vaccination and Challenge

A total of 420 channel catfish fry were vaccinated by DI as described above except for using only the experimental vaccine 17-23 and FCRR at concentrations of $6.7 \times 10^4$ and $5.7 \times 10^7$ CFUmL$^{-1}$, respectively for 30 min. A control group was sham vaccinated by immersion in sterile modified Shieh broth and exposed to the same procedures and the same environmental conditions as the vaccinated fish except for the addition of an active vaccine ingredient. Three treatments/four replicates each. Following vaccination, the vaccinated or sham vaccinated fry in each treatment group were replaced back into their holding aquaria and were fed 2-3 times daily at ~3-4 percent body weight 7 per day until time of challenge. The challenge conditions were the same as that in Trial 1, briefly, at 28 dpv, the fish in each tank were immersion challenged in a 2 L bath containing highly virulent *F. columnare* strain (ALG-530, genomovar II) at a concentration of $9.3 \times 10^6$ CFUmL$^{-1}$ for 30 min. Feeding was resumed 24 h post challenge. Challenged fish were monitored in each tank for 15 days. Dead fish exhibited typical signs of columnaris disease including saddleback and gill lesions were removed twice a day and cultured as described above to re-isolate and confirm *F. columnare* as the cause of death. *F. columnare* was recovered from all the dead fish.

Figure 2:
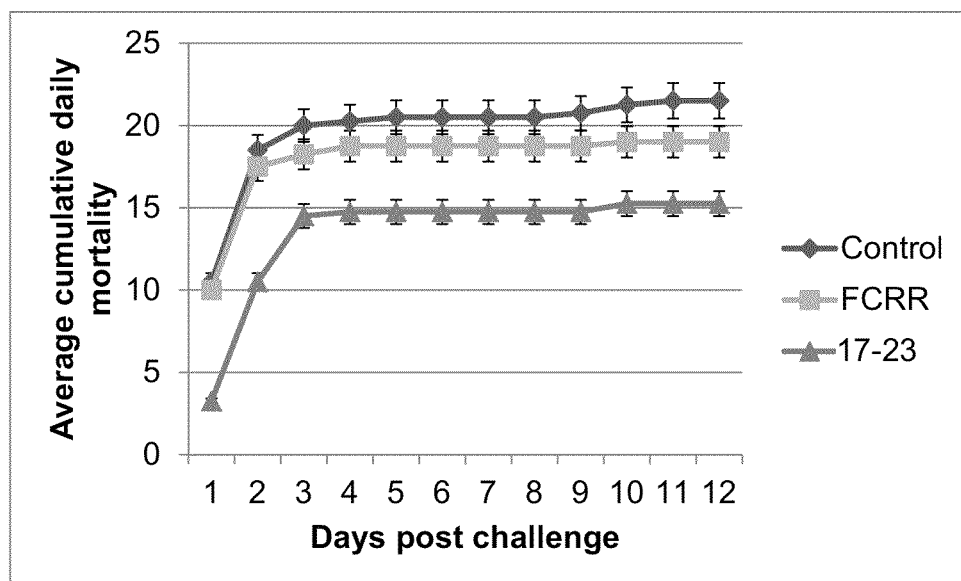
FIG. 2 shows average/mean cumulative daily mortality of catfish fry immersion vaccinated with 17-23, FCRR or sham vaccinated and immersion challenged at 28 dpv with ALG-530 (virulent genomovar II strain of *F. columnare*), cumulative mortalities were calculated from vaccination trial 2.

Similarly, when vaccinated catfish fry were challenged with *F. columnare* ALG-530 at 28 dpv, the cumulative mortality values after 15 days post challenge were 43.6, 54.3 and 61.4% in catfish fry vaccinated with 17-23, FCRR and sham vaccinated, respectively (Table 2). The cumulative mortality observed in the sham vaccinated fry was significantly higher (P<0.05) than the cumulative mortality of fish vaccinated with the genomovar II mutant (17-23) (FIG. 2). RPS values were 29.0 and 11.6% in the fish vaccinated with 17-23 and FCRR, respectively (Table 2).

TABLE 2

Cumulative mortality and relative percent survival of vaccinated channel catfish fry after immersion challenge with virulent *F. columnare* strain at 28 dpv (trial 2). Within a column, different superscript letters means significant difference (p < 0.05).

| Vaccine | Vaccination route | Vaccine dose | Challenge Strain & dose | No. Dead/ challenged | Mortality (%) ± SE | RBS[b] (%) |
|---|---|---|---|---|---|---|
| 17-23 | DI[a] | $6.7 \times 10^6$ CFU/mL | ALG-30 (Genomovar II) | 61/140 | $43.6 \pm 1.62$ [A] | 29.0 |
| FCRR | DI[a] | $5.7 \times 10^6$ CFU/mL | $9.3 \times 10^6$ CFU/mL | 76/140 | $54.3 \pm 0.86$ [AB] | 11.6 |
| Control | DI[a] | Sham vacinated | | 86/140 | $61.4 \pm 0.28$ [B] | — |

[a]DI, direct immersion
[b]RPS, relative percent survival

TABLE 3

Cumulative percent mortality and RPS of vaccinated channel catfish fry after immersion challenge with virulent *F. columnare* strains either genomovar I (ARS-1, challenge dose of $9.8 \times 10^6$ CFU/ml) or genomovar II (BGFS-27, challenge dose of $7.6 \times 10^6$ CFU/ml) at 28 dpv (Experiment 2). Within a column, different superscript letters means significant difference (p < 0.05).

| Mutant Strain | Vaccination Dose (CFU/ml) | Challenge Strain | Cumulative Percent Mortality (mean ± SE) | RPS |
|---|---|---|---|---|
| 17-23 | $6.5 \times 10^6$ | ARS-1[a] | $1.5 \pm 0.01$[a] | 90.9 |
| | | BGFS-27[b] | $41.5 \pm 0.08$[b] | 37.0 |
| FCRR | $6.3 \times 10^6$ | ARS-1[a] | $4.5 \pm 0.01$[a] | 72.7 |
| | | BGFS-27[b] | $63.0 \pm 0.05$[c] | 4.4 |
| Control | — | ARS-1[a] | $16.5 \pm 0.03$[a] | — |
| | | BGFS-27[b] | $65.9 \pm 0.03$[c] | — |

[a]genomovar I *F. columnare*
[b]genomovar II *F. columnare*
[c]RPS, relative percent survival

Example 3

Nile Tilapia Vaccination and Challenge

A total of 510 Nile tilapia fingerlings were distributed into three treatment groups, 170 fish were used in each group (17 fish per aquarium, ten replicates). Tilapia were vaccinated by DI as described in Example 2, using the experimental vaccine 17-23 and FCRR at concentrations of $2.2 \times 10^6$ and $7.3 \times 10^6$ $CFUmL^{-1}$, respectively for 30 min. A control group was sham vaccinated by immersion in sterile MS broth and exposed to the same procedures and the same environmental conditions as the vaccinated fish except for the addition of an active vaccine ingredient. The vaccination suspension was two liters of water+20 mL of the corresponding mutant culture or sterile MS for the control fish. After vaccination, the fish in each treatment group were removed from the vaccine bath, replaced back into their original holding aquaria according to their respective treatment group until challenge date, and daily fed 3% body weight. At 28 dpv, the fish in each treatment group were divided into 2 groups, 5 replicates/aquaria each. The fish in each group were immersion challenged in a bath containing either F. columnare strain (BGFS-27, genomovar II) or (ARS-1, genomovar I) at concentrations of $2.7 \times 10^6$ or $5.5 \times 10^6$ $CFUmL^{-1}$, respectively for 30 min. Feeding was resumed 24 h post challenge. Challenged fish were monitored for fifteen days post challenge and mortalities were recorded daily. Dead fish were removed twice every day and cultured to confirm presence or absence of F. columnare in the dead fish as the cause of death. Bacterial cultures were derived from the skin and gill tissues and streaked onto MS tobramycin agar plates. Results of challenge were presented as RPS.

Figure 3:
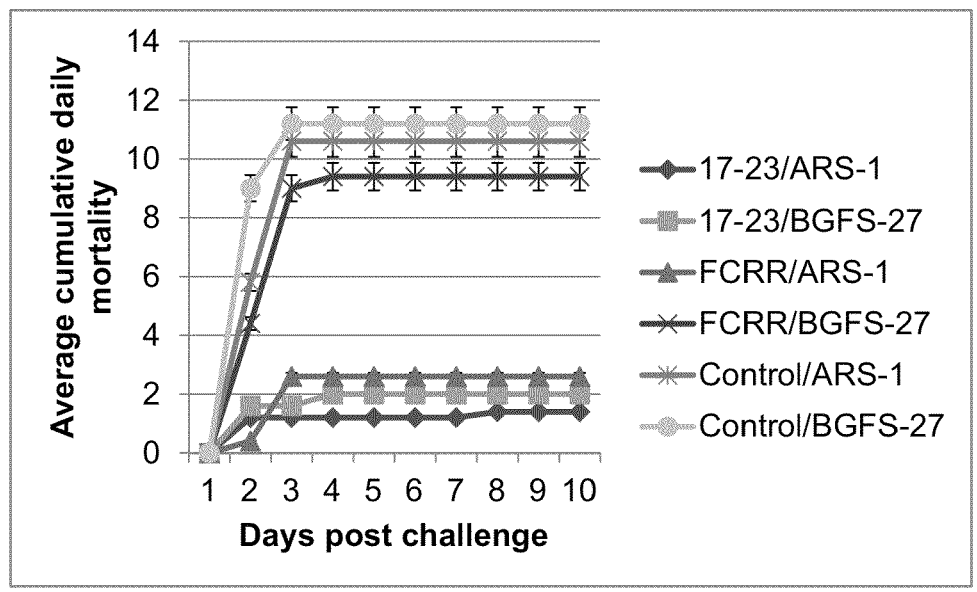
FIG. 3 shows average/mean cumulative daily mortality of Nile tilapia immersion vaccinated with 17-23, FCRR or sham vaccinated and immersion challenged at 28 dpv with either BGFS-27 (genomovar II strain of *F. columnare*) or ARS-1 (genomovar I strain of *F. columnare*), cumulative mortalities were calculated from vaccination trial 3.
Figure 4:
FIG. 4 (left panel) Zebrafish (*Danio rerio*), (middle panel) channel catfish (*Ictalurus punctatus*) and (right panel) Nile tilapia (*Oreochromis niloticus*) showing characteristic lesions of columnaris disease.

When vaccinated Nile tilapia with 17-23, FCRR or sham vaccinated were challenged with BGFS-27, genomovar II F. columnare, at 28 dpv, the cumulative mortality was 11.8, 55.3 or 65.9% respectively (Table 4). While the cumulative mortality was 8.2, 15.3 or 62.4% when the vaccinated tilapia with 17-23, FCRR or sham vaccinated respectively, were challenged with ARS-1, genomovar I F. columnare, at 28 dpv. The cumulative mortality observed with sham vaccinated fish challenged with either genomovars and the cumulative mortality observed in fish vaccinated with FCRR challenged with BGFS-27, genomovar II, were significantly higher ($p<0.05$) than the cumulative mortality observed with fish vaccinated with 17-23 challenged with either genomovars and the cumulative mortality observed with fish vaccinated with FCRR challenged with ARS-1, genomovar I (Table 3). The cumulative mortalities of genomovar II mutant vaccinated fish were significantly ($P<0.05$) lower than those of MS sham vaccinated fish (FIG. 3), suggesting that this mutant provided significant protection to Nile tilapia against wild type virulent F. columnare strain. After 15 days post challenge, RPS values of 82.1 and 16.1% were observed in vaccinated Nile tilapia with 17-23 and 10 FCRR, respectively, when the fish were challenged at 28 dpv with BGFS-27, genomovar II strain of F. columnare (Table 2). However, when the vaccinated fish with 17-23 and FCRR were challenged with ARS-1, genomovar I strain of F. columnare at 28 dpv, RPS values were 86.9 and 75.5%, respectively (Table 3). F. columnare were re-isolated from skin and gills of dead fish. Similar to results of trial 1 and 2, vaccination of Nile tilapia with the genomovar II mutant/vaccine, 17-23, conferred protection against virulent F. columnare strains of both genomovars (I and II) as revealed by significant differences in cumulative mortality between treatment groups (FIG. 3).

TABLE 4

Cumulative mortality and relative percent survival of immersion vaccinated Nile tilapia fingerlings after immersion challenge with either genomovar I or genomovar II F. columnare strains at 28 dpv (trial 3). Within a column, different superscript letters indicates significant difference ($p < 0.05$).

| Vaccine | Vaccine dose | Challenge Strain | Challenge dose | No. Dead/challenged | Mortality (%) ± SE | RBS[b] (%) |
|---|---|---|---|---|---|---|
| 17-23 | $2.2 \times 10^6$ CFU/mL | ARS-1[a] | $5.5 \times 10^6$ CFU/mL | 7/85 | $8.2 \pm 0.63$ [A] | 86.9 |
|  |  | BGFS-27[b] | $2.7 \times 10^6$ CFU/mL | 10/85 | $11.8 \pm 1.58$ [A] | 82.1 |
| FCRR | $7.3 \times 10^6$ CFU/mL | ARS-1[a] | $5.5 \times 10^6$ CFU/mL | 13/85 | $15.3 \pm 1.20$ [A] | 75.5 |
|  |  | BGFS-27[b] | $2.7 \times 10^6$ CFU/mL | 47/85 | $55.3 \pm 0.36$ [B] | 16.1 |
| Control | Sham vaccinated | ARS-1[a] | $5.5 \times 10^6$ CFU/mL | 53/85 | $62.4 \pm 0.85$ [B] | — |
|  |  | BGFS-27[b] | $2.7 \times 10^6$ CFU/mL | 56/85 | $65.9 \pm 0.47$ [B] | — |

[a] genomovar I F. columnare
[b] genomovar II F. columnare
[c] RPS, relative percent survival

Example 4

Adhesion Experiment

Figure 5:
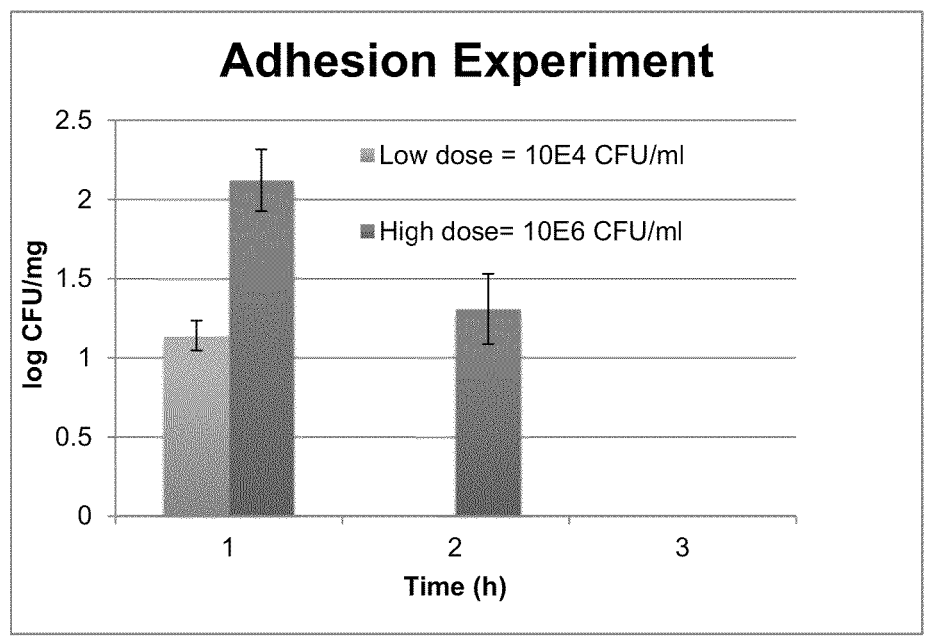
FIG. 5 is a graph presenting the adhesion study data.

Fish (~4 g tilapia×30 fish per dose) were exposed to two doses of the vaccine: $1.7 \times 10^4$ CFU/ml and $1.7 \times 10^6$ for 30 min (exposure was conducted as per the above-described challenge protocol). Gill clips were taken from 3 randomly selected fish at 30 min post-immersion in the vaccine bath, and at 6 and 24 h post immersion (fish were moved from the vaccination bath to their original tanks after 30 min of exposure). Three samples (1 sample=3 fish) were analyzed per sampling time. Gill tissue was weighed and diluted in 500 µl of MS broth, homogenized with a hand-held tissue homogenizer, and serially diluted in MS broth. From each dilution, 100 µl was plated onto 3 MS agar plates, and incubated for 48 h at 28° C. Colonies were counted, and the average CFU/mg are presented in FIG. 5. According to the graph, there was a dose response at 30 min post-immersion, and vaccine was recovered from the high dose at 6 h, but only a few cells were recovered from the $10^6$ CFU/ml dose at 24 h. Per the counting protocol, fewer than 30 colonies per plate were annotated as "zero."

Discussion.

The commercial AQUAVAC-COL™ vaccine has an avirulent rifampicin-resistant mutant of *F. columnare* genomovar I (relatively less virulent as compared with genomovar II). As disclosed herein, the efficacies of the new attenuated mutant genomovar II *F. columnare* strains (17-23 and 16-534), and the commercial vaccine, were evaluated in three different fish species. The results indicate the attenuated strains were safe and provided protective (varied across fish species) immunity against subsequent challenge. For example, vaccination of zebrafish with 17-23, 16-534 and FCRR at concentrations of $7.8 \times 10^6$, $1.5 \times 10^6$ and $9.1 \times 10^6$ CFUml$^{-1}$, respectively, resulted in 63.1%, 70.2% and 81.0% cumulative mortality and 28.4%, 20.3% and 8.1%, RPS, respectively, following challenge with BGFS-27 (genomovar II) at 28 dpv. The 17-23 strain performed significantly better than the commercial vaccine.

Overarching Conclusion.

When the fish were challenged with BGFS-27, cumulative mortality values were 11.8, 55.3 and 65.9% for 17-23, FCRR and control, respectively and RPS values were 82.1 and 16.1% for 17-23 and FCRR, respectively. Although, when the fish were challenged with ARS-1, cumulative mortality values were 8.2, 15.3 and 62.4% for 17-23, FCRR and control, respectively and RPS values were 86.9 and 75.5% for 17-23 and FCRR, respectively. Overall, the results demonstrated that the experimental vaccine 17-23 outperformed FCRR in protecting fish against subsequent challenge to highly virulent strains of *F. columnare*, and indicates that administration of genomovar II mutants as potential live-modified vaccines is safe and elicits greater protection against columnaris disease than the use of genomovar I mutants.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An attenuated *Flavabacterium* spp. strain suitable for use as an active component of a safe and effective immunological composition, which is suitable for eliciting in a fish an immune response against at least one virulent *Flavobacterium* spp. wherein the strain is selected from the group consisting of strain 17-23 deposited as CECT 7737, and strain 16-534 deposited as CECT 7736.

2. A safe and effective immunological composition comprising at least one attenuated strain of a genomovar II *Flavobacterium* spp., wherein the attenuated strain is resistant to rifampicin, and wherein the attenuated strain is capable of eliciting an immune response in fish against a subsequent natural exposure to, or experimental challenge with, at least one virulent *Flavabacterium* ssp. strain, wherein the attenuated strain is selected from the group consisting of strain 17-23 deposited as CECT 7737, and strain 16-534 deposited as CECT 7736.

3. The composition of claim 2, wherein the composition is a vaccine composition, which is capable of eliciting a protective immune response in fish against a subsequent natural exposure to, or experimental challenge with, at least one virulent *Flavabacterium* ssp. strain.

4. The composition of claim 2, further comprising a pharmaceutically or veterinarily acceptable carrier.

5. The composition of claim 2, further comprising a stabilization buffer.

6. The composition of claim 5, wherein the stabilization buffer comprises:
   a. $FeSO_4$;
   b. $CaCl_2$;
   c. $KH_2PO_4$; and
   d. $MgSO_4$.

7. The composition of claim 5, wherein the stabilization buffer comprises:
   a. about 0.4 µM $FeSO_4$;
   b. about 4.6 µM $CaCl_2$;
   c. about 100 µM $KH_2PO_4$; and
   d. about 120 µM $MgSO_4$.

8. The composition of claim 5, wherein the buffer stabilizes the composition for at least about two months when the composition is stored at ambient temperature.

9. A method of inducing protective immunity in fish against exposure to, or experimental challenge with, virulent strains of genomovar I or II *Flavobacterium* spp., comprising the step of administering to said fish the composition of claim 2, thereby inducing the protective immunity.

10. The method of claim 9, wherein the virulent strain is either a genomovar I or II *F. columnare*.

11. The method of claim 9, wherein the fish is a freshwater fish.

12. The method of claim 9, wherein the fish is a tilapia, a catfish, a zebrafish a salmon, a trout, a carp, a tuna or a shellfish.

13. The method of claim 9, wherein the administration is by immersion vaccination.

14. A method for producing the composition of claim 5 comprising the stabilization buffer, the method comprising the step of re-suspending the at least one attenuated *Flavobacterium* spp. strain in the stabilization buffer.

15. The method of claim 14, comprising the steps of:
   a. growing the attenuated *Flavobacterium* spp. strain in a medium and pelleting the *Flavobacterium* spp. strain by centrifugation at approximately 5,000 rpm for 5 minutes;
   b. removing the medium;
   c. re-suspending the *Flavobacterium* spp. strain in the stabilization buffer;
   d. transferring the resuspended cells to a sterile container, thereby producing the composition comprising the stabilization buffer.

* * * * *